United States Patent [19]

Smith

[11] Patent Number: 4,522,068

[45] Date of Patent: Jun. 11, 1985

[54] ULTRASONIC DENSITOMETER FOR LIQUID SLURRIES

[75] Inventor: George E. Smith, Missouri City, Tex.

[73] Assignee: Electro-Flow Controls, Inc., Missouri City, Tex.

[21] Appl. No.: 553,585

[22] Filed: Nov. 21, 1983

[51] Int. Cl.³ .............................................. G01N 9/24
[52] U.S. Cl. ..................................... 73/32 A; 73/597
[58] Field of Search ................................ 73/32 A, 597

[56] References Cited

U.S. PATENT DOCUMENTS

| | | | |
|---|---|---|---|
| 3,983,744 | 10/1976 | Agar | 73/32 A |
| 4,208,906 | 6/1980 | Roberts | 73/597 |
| 4,235,099 | 11/1980 | Ishizaka | 73/32 A |
| 4,362,048 | 12/1982 | Agar | 73/32 A |
| 4,442,700 | 4/1984 | Swoboda | 73/32 A |

Primary Examiner—James J. Gill
Attorney, Agent, or Firm—Vaden, Eickenroht, Thompson & Jamison

[57] ABSTRACT

Apparatus employing ultrasonic pulse production at a transmit transducer at a known frequency is received at a receive transducer for sampling a liquid slurry of known composition, but unknown ratio, makeup of liquid, gas and fine, suspended particles. The transmission time is converted to digital form and an adjustable velocity-density slope factor is applied from empirical data to result in a readout voltage that directly relates to the density of the liquid slurry.

4 Claims, 1 Drawing Figure

U.S. Patent   Jun. 11, 1985   4,522,068
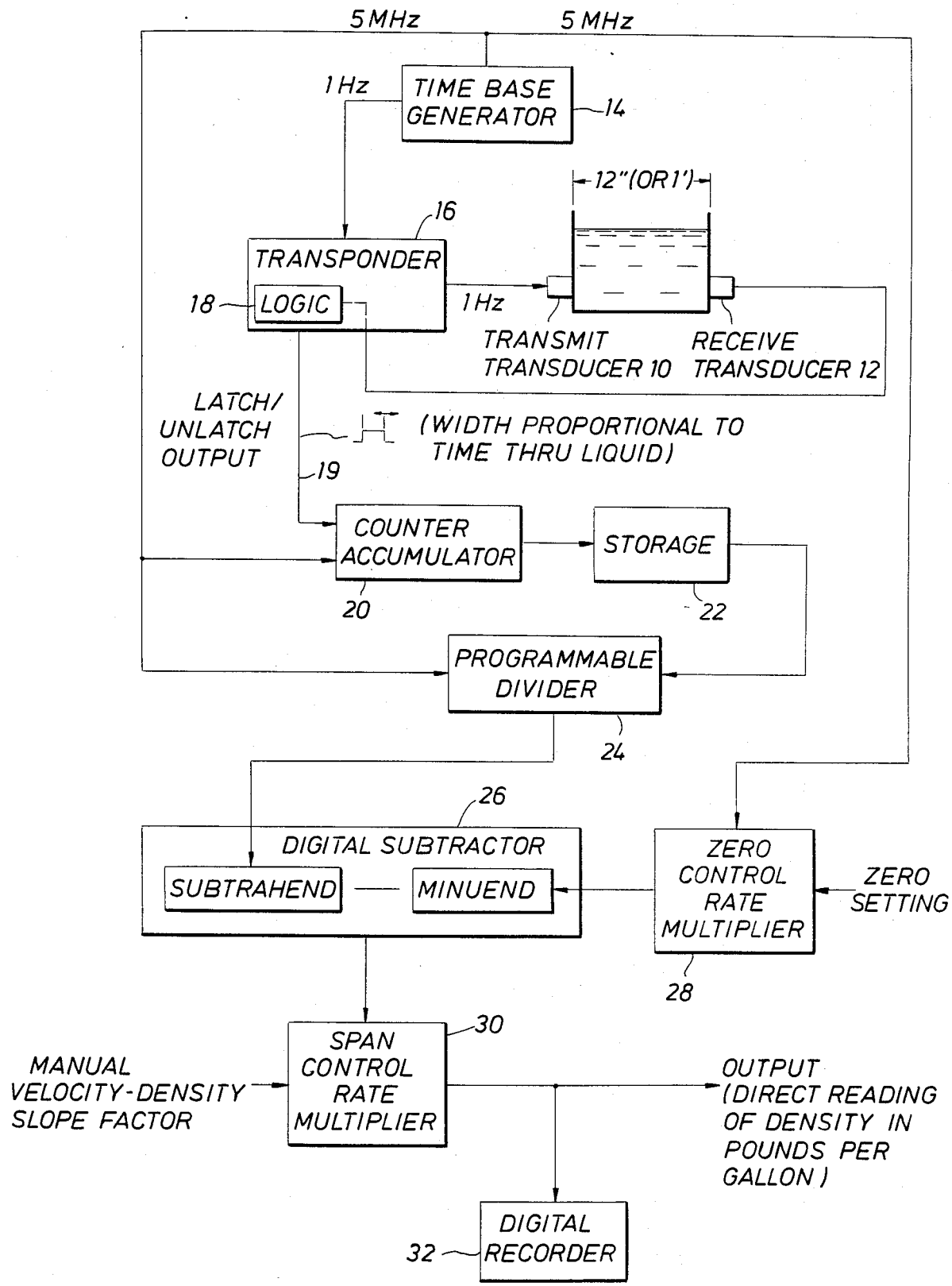

ULTRASONIC DENSITOMETER FOR LIQUID SLURRIES

BACKGROUND OF THE INVENTION

1. Field of the Invention

This invention pertains to fluid density measurements and more particularly to high frequency acoustical signal velocity measurements of fluid slurries comprising a mixture of liquids, gases and solid particulates, the ratio therebetween being unknown.

2. Description of the Prior Art

Density measurements of fluids employed in oil well drilling, completion and cementing are integral and necessary in the successful and efficient performance of these operations. Accurate observation and monitoring of drilling mud density has generally been a manual, largely "off-line" operation. The most common device for density determination is the simple mud balance scale, wherein drilling rig personnel periodically scoop up a small mud sample, weigh it on a commercially available scale designed for that purpose (which scale correlates weight to density or at least weight change to density change), and record the reading in the drilling log book. Hourly readings are usually also entered into the driller's report. The readings are informative and are the basis for adjusting the constituent parts or otherwise modifying the fluid makeup when the reading varies from acceptable limits.

There have been attempts to automate the above process using both pneumatic and electronic means. For example, one technique that has been employed with a limited degree of success employs differential pressure in a mud reservoir. However, such a technique, although theoretically feasible, is very susceptible to mud caking. Bouyancy techniques in general are also susceptible to inaccuracies resulting from solids settling and to motion distortion. Radioactive measurements have also been employed, but such techniques are both expensive and hazardous. Most techniques also require that they be employed in the first reserve pit after most of the solids and entrained gases are removed. Therefore, the measurements are not realistic of the actual operating fluid conditions and are capable of being made long after the conditions may have changed.

Densitometers using electronic means have been concerned generally with measuring density changes of fluid whose constitutent parts are a combination of liquids or a combination of liquids and entrained gas. It is known that by measuring the acoustic impedance of such a fluid, the density can be determined. The most common type of densitometer utilizing this principle employs a resonant mechanical component, whose resonant point is determined in part by the fluid being measured. This frequency then correlates to acoustic impedance which, in turn, correlates to density. It is known that the resonant frequency decreases with density and that at high fluid densities, which are normally encountered in drilling fluid slurries, the acoustic impedance is relatively constant. Thus, such densitometers are virtually inoperable for making meaningful measurements in the environment of drilling fluids even though acceptable in the environment of lighter, cleaner and more well-defined pipeline fluids.

Ultrasonics have previously been employed in experiments for making density measurement purposes. Again, using fluids comprising liquid and gas mixtures, it has been possible to measure the length of time for a high frequency pulse to pass through a predetermined distance of the fluid. The more dense the fluid, the faster the propagation of the pulse. Hence, it has been possible to correlate travel time to density in such a fluid.

However, the use of ultrasonics in slurry type drilling fluids have not been successful. The major problems appear to be overcoming the dispersion of the transmitted pulse as it encounters the microscopically fine particles of the extremely dense solid materials in the fluid, typically particles of barite. To appreciate the problems associated with developing an automatic, and continuous process for measuring drilling mud density, consider the overall character of drilling mud.

Mud consists generally of a liquid vehicle, usually water, oil or diesel fuel, and contains thickening and weighting ingredients of a ground, fine-flour consistency. Furthermore, the drilled solids of varying size and density circulate in the mud, as do entrained air and gas, as well as varying amounts of salt and fresh water encountered during the drilling process. If permitted to remain still, mud tends to "gel" and suspended solids will, in time, settle out or build up on wetted surfaces. Despite vigorous agitation, mud can typically develop "strata" of varying density in the mud tank system. Drilling mud varies in consistency depending on additives and bottom hole conditions from light, easily flowing mud of table cream consistency to the heavy consistency of grease that barely flows when pumped. Mud thickness also varies with liquid temperature and its chemical make-up. Thick muds are known to be a problem in clogging mechanical apparatus and the high pH of most muds tend to corrode all materials except stainless steel.

It has also been true that anything in contact with drilling fluid normally experiences a build up on the wetted surface that are temporarily exposed to air. This build up has frustrated mechanical designers in attempting to employ bouyancy sensors, differential pressure sensors, continuously-flushed mechanical scales, and other methods of sensing mud density. Rotary joints tend to stick, balance devices tend to gum up and sensitive pressure sensors are battered by the turbulence of mud agitators which have been employed. Therefore, it was recognized by the inventor herein that it would be greatly advantageous to avoid the mechanical difficulties of measuring density using devices with those commonly employed in the prior art. Ultrasonic frequency signals which were not felt to be acceptable for use with mud systems, has been adapted as hereinafter described by the inventor in a novel and unique manner to effectively overcome the difficulties described above.

Therefore, it is a feature of the present invention to provide an improved ultrasonic frequency densitometer for the measurement of the density of drilling fluids, completion fluids and fluids of like consistency, which densitometer is usable under the rugged conditions that exist in the oil field and similar environmental situations.

Another feature of the present invention is to provide an improved method of measuring a minimum number of parameters of a fluid, utilizing a system with no moving mechanical parts, for deriving sufficient information for practical and accurate determination of fluid density.

Yet another feature of the present invention is to provide for the improved utilization of digital processing circuitry for all mathematical computations, which minimizes or eliminates calculation efforts, even under rugged environmental conditions.

Yet another feature of the present invention is to provide for the utilization of ultrasonic wave impulses for the measurement of acoustic velocity of sound waves in a liquid slurry comprising fluid and minute solid particles and the utilization of sound velocity information for the calculation and display of the slurry density.

SUMMARY OF THE INVENTION

The method and apparatus disclosed herein utilizes the "fast wave" or leading edge of the received compression wave resulting from a transmitted pulse into the fluid slurry whose density is being measured. A quantity of the fluid is isolated between a transmit transducer and a receive transducer, the two transducers being set at a predetermined distance from one another. Pulses at a predetermined ultrasonic frequency are used to drive the transmit transducer. A latching output signal is produced with the development of each transmit pulse and an unlatching output signal is produced with the receipt of the leading edge of the compression wave relating thereto as it is received by the receive transducer. The time between the latching and the unlatching occurrences is determined in digital fashion using a high frequency counting scheme. The count is correlated against an empirically developed standard as an indication of density.

The empirical measurements show that in a fluid slurry type of mixture, which is a combination of a known liquid and a solid of very fine suspended particles of known character, the more dense the mixture, the slower the movement of the transmission compression wave front through the fluid. A master scale for correlating a fluid slurry of similar composition makeup can be made by changing, under controlled conditions, the mixture ratio of liquid to solid and recording the resulting transmission times. Field measurements of the fluid slurry under measurement can then be corrected by using an empirical slope factor from the master scale for accurate density determination.

BRIEF DESCRIPTION OF THE DRAWING

So that the manner in which the above-recited features and advantages of the invention, as well as others which will become apparent, are attained and can be understood in detail, more particular description of the invention briefly summarized above may be had by reference to the embodiment thereof which is illustrated in the drawing, which drawing forms a part of this specification. It is to be noted, however, that the appended drawing illustrates only a preferred embodiment of the invention and is therefore not to be considered limiting of its scope, for the invention may admit to other equally effective embodiments.

In the drawing:

The FIGURE is a simplied block diagram of a preferred apparatus embodiment of the present invention.

DESCRIPTION OF THE PREFERRED EMBODIMENT

A pulse or compression wavefront of ultrasonic energy, when passing through a fluid slurry, encounters literally millions of interface transitions from solid to liquid and from liquid to solid. Although much of the energy diffuses in a lateral direction, there is a "fast wave" that travels in the original direction straight through to the opposite side to where the energy is detected. However, it has been determined by empirical data that the more transitions there are, which means the thicker or denser the fluid slurry is, the slower the travel time is for the fast wave. The theory is that there is an overall slowing of the wave front caused by the transitions. That is, the slow-down transitions are greater in overall effect than are the speed-up transitions.

It should be further noted that there is a great deal of amplitude attenuation in the signal and that there are many signal wave segments received after rebound reflection following receipt of the "fast wave", but the fast wave signals or the highest velocity signals are the ones that carry the density measurement information. However, it is also true there is information which is contained in the subsequent portion of the wave beyond the "fast wave", as will be explained hereafter.

The generalized formula with which the system to be described hereinafter for determining the density of such fluids as a drilling fluid slurry from the "fast wave" ultrasonic velocity information is shown by the following equation:

$$D = [(V_B - V_L) \cdot S] + D_B$$

wherein, D equals the density in pounds per gallon; $V_L$ equals the sound velocity of the fluid slurry in feet per second; $V_B$ equals a base velocity for "clean" fluid in feet per second; S equals the velocity-density slope factor in pounds per gallon per feet per second; and $D_B$ equals the density in pounds per gallon for "clean" base fluid.

Now referring to the FIGURE, a simplified block diagram is shown of suitable apparatus in accordance with the present invention. An ultrasonic transmit transducer 10 is placed at a predetermined distance, for example 12 inches, from a corresponding ultrasonic receive transducer 12. The area between the transducer includes an isolated sampling of the fluid slurry undergoing density measurement. This isolation can be accomplished by setting off a fluid quantity with a vessel which forms an isolated sampling of the larger quantity of fluid, or the transducers can be joined by a U-shaped holder or bracket that does not interfere with the straight-through transmission path therebetween.

A time base generator 14 is used to produce a 1 Hz clock signal to transponder 16, which produces a sharply spiked-shaped pulse signal at 1 Hz intervals to transmit transducer 10. The transponder also includes a flip-flop or other similar logic circuit 18 for producing a latch output or leading edge of a square wave output 19 to counter-accumulator 20 simultaneously with the production of the transmit pulse to transmit transducer 10. A preferred circuit for the ultrasonic transponder is Part No. E-201 manufactured by Massa Products Corp. Receive transducer 12 is connected to logic circuit 18 and produces an unlatch or trailing edge of the square wave output with the receipt of the "fast wave" through the isolated fluid sample. Ultimately the period of the square wave, or the distance between the latch or leading edge and the unlatch or trailing edge of the output from the logic circuit, is a measure of the fluid slurry density. A preferred transducer for transducers 10 and 12 are piezoelectric ultrasonic crystal transducers, as more fully described hereinafter.

The ultrasonic transmit transducer and receive transducer are similar, each being designed from a piezoelectric ceramic crystal for converting electrical energy into ultrasonic acoustic pulses (for the transmit transducer) or for converting the received ultrasonic acoustic energy pulses into electrical energy (for the receive transducer). A metallic focusing "lens" can be employed with the transmit transducer crystals for focusing purposes so as to concentrate the "fast wave" compression wave in an intense, parallel ultrasonic wavefront across the fluid sample to the receive transducer. The receive transducer can have a similar focusing funnel "lens". The time lapse in the lenses is accommodated electronically in the base or zero setting control described hereafter. Such lenses also help protect the transducers by sealing their faces against rough treatment that can be present in the mud pits.

The output logic device 18 is applied to counter-accumulator 20 with the original 5 MHz clock signal in the form of pulses. The existence or presence of the latch or leading edge of square wave output 19 establishes a base time for the counter, which accumulates counts of the clock pulses until the receipt of the trailing edge of square wave output 19 terminates the accumulated count and transfers the count to storage device 22. A preferred storage device is represented by a series of latches as included in Motorola MC 14508 chips. The number stored in the counter represents the transmit time of the "fast wave" of ultrasonic energy through the liquid in digital form. The stored number is applied to the programming inputs of a programmable divider chip 24, preferably model RCA CD4059, which also receives the 5 MHz clock pulses from the time base generator, to divide the count by a number that is proportional to the transit time of ultrasonic energy through the fluid. The output frequency from this chip is directly proportional to the sonic velocity and can be used to operate an appropriate readout. For example, if the propagation velocity is 1250 feet per second, the output frequency from the programmable divider is 1250 Hz.

The output frequency from programmable divider 24 is applied to the subtrahend input of digital subtractor 26. The minuend input to the digital subtractor is from zero control rate multiplier 28, which can be conveniently constructed from a chain of Motorola MC 14027 integrated circuit chips and BCD code-entry switches. The rate multiplier also receives the original 5 MHz signal from time base generator 14 and multiplies this signal by a number, which can be either more or less than "1", which is established in the BCD switches. The resulting output frequency is entered into the minuend of the digital subtractor for subtracting from the velocity frequency number in the subtrahend. The number in the minuend is representative of a zero setting and can be set in by a manual setting control. This setting is used to set in the base density number, $D_B$, and can be used to compensate for such things as less than a perfect set-up dimensioning between the transducers. Further, the zero setting permits field calibration of the system since rough handling and other factors in set up could vary factory adjustments. A change in the basic class of drilling fluid will also require a change in the zero setting.

The difference frequency from the digital subtractor is applied to another rate multiplier, in this case, span control rate multiplier 30, also fed by a set of BCD switches for entry of a multiplier factor. The number supplied to rate multiplier 30 represents the velocity-density slope, usually negative, as determined by empirical data. By judicious choice of the multiplier number here and to rate multiplier 28 by the technician, the output from multiplier 30 can be made directly proportional to fluid density. For example, in a preferred embodiment of the present invention, a 0–2000 pulse per second output can be made representative of a 0–20 pounds per gallon fluid density. As the density measurement moves out of this range, the slope factor may have to be changed from the empirically determined data, but this is readily accomplished either by a manual resetting or automatically by employing a slope reader connected as the input to rate multiplier 30.

The output from rate multiplier 30 can be applied to any convenient frequency display device or operating circuit.

The type of readout that is preferable is a liquid-crystal display, which is easily read in the brightest sunlight. Furthermore, the addition of a simple frequency-to-analog conversion circuit produces an output voltage directly to the input of a common chart recorder 32, thus producing a continuous permanent record of fluid density plotted against time.

The signals resulting from multiplier 30 can also be interfaced with computerized drilling or monitoring systems. Also, although English units are mentioned above, conversion to metric units can be accomplished with ease.

A change in the base fluid will cause the change in the master velocity-density curve and hence the slope factor input to rate multiplier 30. Likewise, a change in the solid additive will change the velocity-density curve. However, once the makeup composition of liquid and solid is known, then the proper velocity-density curve information can be determined, selected and employed.

Please also note that threshold level devices can be connected to such output voltage for operating automatic adjustment equipment to change the ratio of the mixture of the fluid slurry, for operating alarms and the like.

Please note that the system just described is also particularly well-suited for monitoring higher density fluids encountered in drilling and cementing operations, where the thermal coefficient of expansion of such slurries is relatively small as compared with the thermal coefficient of expansion of light hydrocarbons.

It should be apparent that there are some changes of fluid mixture that could occur in addition to merely a change in fluid-to-solid ratio. These include gas being entrained into the fluid or larger solids or cuttings resulting from a drilling operation being circulated in the fluid in addition to the intended barite or other additive. The detection of these phenomena is achieved by observing the portion of the wavefront signal developed at the receive transducer. A fairly homogeneous solution will cause the rebounding segments of the transmission wave to randomly arrive at the receive transducer to form a "noise" response of gradually decaying shape (discounting the "shear" wave which arrives at a predictable time following the compression wave). However, a gas pocket, or a large solid particle, will show up as an irregularity or aberration that is quite noticeable. The "fast wave" is not appreciably affected, however. Further, a settling out of the gas or large solid will show up with subsequent samplings as the waveform at the receive transducer calms down to the predictable form described above.

Any mud tank system will experience build up. Since the ultrasonic transducers described herein operate totally submerged and have no moving parts, mud buildup rarely occurs to the extent that operation will be affected. If a tank empties and a mud coating dries on the transducer, it will dissolve when the tank is refilled. When the mud level again covers the transducer, fluid from the tank mud will fill the pore spaces of the dry mud. Ultrasonic energy easily penetrates normal crusts even before it dissolves, which, of course, closely matches in fluid density with the density of the fluid in the mud tanks.

While drilling and cementing applications have been discussed as being typical applications for the apparatus described above, fluid density measurements can also be made using such apparatus in such diverse applications as coal washing, wastewater treatment, sewage sludge measurements, and pulp and paper mill operations and others.

While a particular embodiment of the invention has been shown and described, it will be understood that the invention is not limited thereto, since modifications may be made and will become apparent to those skilled in the art.

What is claimed is:

1. A method for directly measuring the density of a mixture of a fluid and a solid of fine, suspended particles of known character, comprising,
   isolating a quantity of the fluid between a transmit transducer and a receive transducer separated by a predetermined distance,
   driving said transmit transducer with pulses at a predetermined frequency,
   receiving said pulses by said receive transducer following the acoustic time of transmission through said isolated fluid,
   producing a latching/unlatching output signal having a leading edge occurring with each produced pulse supplied to said transmit transducer and a trailing edge occurring with each received pulse received by said receive transducer,
   accumulating a count from a high frequency standard signal during the period between said leading edge occurrence and said trailing edge occurrence,
   storing said accumulated count,
   dividing said stored count by a number of proportional to a measurement conversion standard to produce a high frequency velocity signal,
   subtracting a fixed high frequency signal from said high frequency velocity signal, said fixed high frequency signal representing a frequency corresponding to the lowest expected fluid density, to produce a subtraction frequency corresponding to a fluid density velocity below the velocity for the lowest fluid density, and
   multiplying said subtraction frequency with an empirically determined span factor to produce an output in density units of measurement.

2. A method for directly measuring the density of a thick fluid slurry comprised of particles of unknown gases, liquids and solids mixed into a clean slurry, the clean slurry being comprised of a known amount of finely ground particulates of a known thickening ingredient suspended in a known liquid vehicle, which comprises
   isolating a quantity of the fluid slurry between an electronic transmit transducer and a corresponding receive transducer separated from said transmit transducer by a predetermined distance,
   determining the length of time for a signal of predetermined transmit frequency to travel from said transmit transducer to said receive transducer, and
   correlating said travel time to an experience curve of travel time versus density for the clean slurry, which density-to-time curve shows a decrease in the speed of the signal with an increase in fluid slurry density.

3. The method in accordance with claim 2, and including detecting at said receive transducer the leading edges of the transmitted pulses for making the travel time measurements.

4. The method in accordance with claim 2, and including, after the isolation step, driving said transmit transducer with pulses at a predetermined frequency rate.

* * * * *